United States Patent [19]

Simonet-Haibe

[11] 4,095,599

[45] Jun. 20, 1978

[54] DEVICE FOR COLLECTING BODY EXCRETIONS AND METHOD OF USING SAME

[75] Inventor: Denise Simonet-Haibe, Paris, France

[73] Assignee: Laboratoires Biotrol Societe Anonyme, Paris, France

[21] Appl. No.: 757,915

[22] Filed: Jan. 10, 1977

[30] Foreign Application Priority Data

Feb. 18, 1976 France .................................. 76 04474

[51] Int. Cl.² ................................................ A61F 5/44
[52] U.S. Cl. .................................................... 128/283
[58] Field of Search ........ 128/283, 294, 295, DIG. 24

[56] References Cited

U.S. PATENT DOCUMENTS

| | | | |
|---|---|---|---|
| 2,928,393 | 3/1960 | Marsan | 128/283 |
| 3,604,421 | 9/1971 | Pizzella | 128/283 |
| 3,612,053 | 10/1971 | Pratt | 128/283 |
| 3,805,789 | 4/1974 | Marsan | 128/283 |
| 3,827,435 | 8/1974 | Marsan | 128/283 |
| 3,878,847 | 4/1975 | Marsan | 128/294 X |
| 3,897,781 | 8/1975 | Marsan | 128/283 |
| 3,898,990 | 8/1975 | Nolan | 128/283 |

FOREIGN PATENT DOCUMENTS 2,313,064  9/1974  Germany .............................. 128/283

*Primary Examiner*—Robert W. Michell
*Assistant Examiner*—Michael H. Thaler
*Attorney, Agent, or Firm*—Melville, Strasser, Foster & Hoffman

[57] ABSTRACT

A device for draining and collecting body excretions, particularly for post-operative procedures, comprising a gum-based member adapted to be placed in contact with the skin of the user around the location from which the excretion is to be discharged, the member having a hole enabling the free flow of excretion therethrough, a support on which a bag for collecting excretion is adapted to be secured, the support being of flexible material and having an aperture larger than the hole in the gum-based member, the support also being provided with pre-cut zones concentric with the aperture for enlarging the size of the aperture, the gum-based member being connected to the support by pushing the portion of the member surrounding the hole through the aperture in the support, thereby forming an annular wrap-around pad tightly embracing the edge of the aperture. Preferably the gum-based member is of Karaya gum mixed with a glycerine binder, and the support is a fabric reinforced resin film.

13 Claims, 6 Drawing Figures

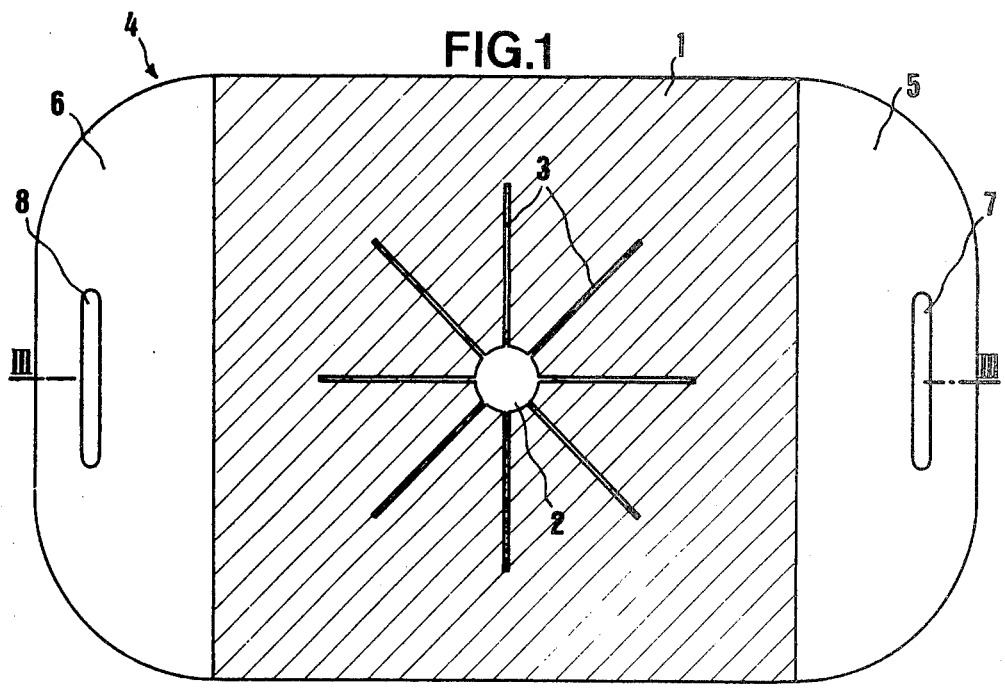
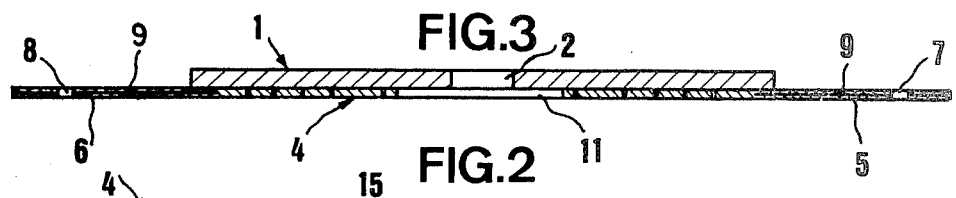
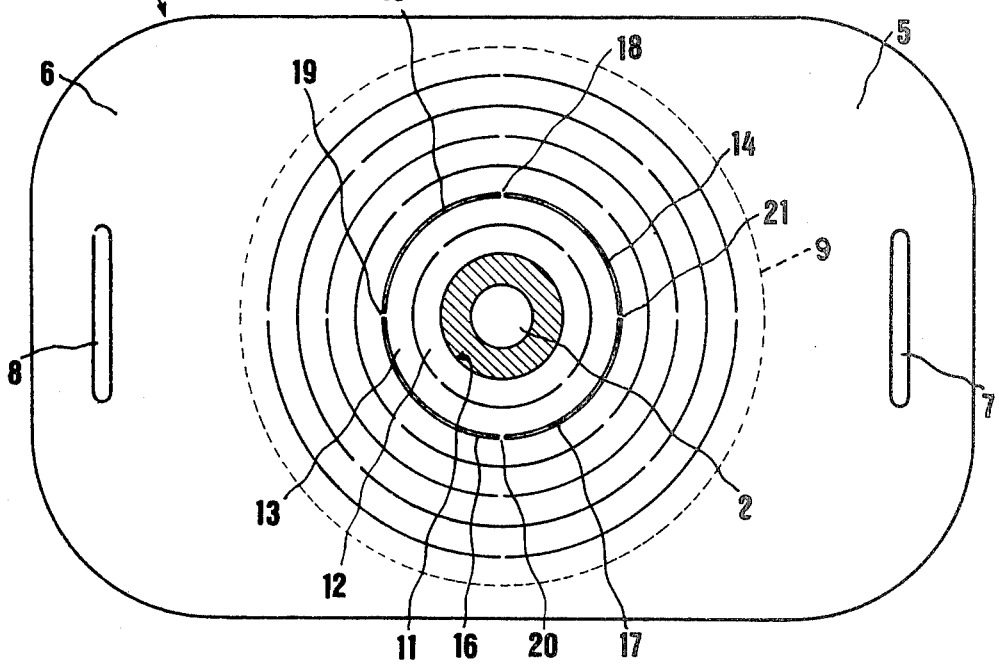

DEVICE FOR COLLECTING BODY EXCRETIONS AND METHOD OF USING SAME

The present invention concerns devices for collecting all kinds of body excretions and more particularly to a device for collecting excretions after an operation.

Plastics bags are already known which collect body excretions of all kinds, particularly for post-operation purposes. Such devices may be used intermittently following an operation or even permanently when, for example, it is an artificial rectum or anus.

At the present time devices of this type comprise a double-faced adhesive member provided with an aperture allowing the free passage of excretions. By one of the faces, the adhesive is fixed to the skin so that the aperture is in relation to the artificial opening in the body and on the other face the adhesive is fixed to a bag of plastic material. Known devices of this type are generally disposable. They are not free of drawbacks.

First of all, the artificial openings of a surgical origin are of a large variety of sizes. The openings, or anastomosis (e.g. in case artificial anus) vary in fact depending on the part of the body which undergoes surgery, the very nature of the patient's tissues and also on the skills of the surgeon. It is therefore difficult to produce collecting devices which adapt themselves to all types of artificial body openings which one comes across in practice. This situation creates very serious drawbacks, for if the diameter of the aperture or device is greater than the transverse diameter of the artificial opening, the excretion may leak out and deposit itself on the patient's skin in the immediately vicinity thereof. Certain excretions are of a very caustic nature for the patient's skin when for example in the case of an artificial anus the surgery was effected in the small intestine where gastric juices still have all their acidity. In such cases the excretions produce intolerable injury to the patient's skin which moreover entails further treatment since the device must be maintained permanently in position.

It is therefore imperative to provide improvements in devices of this type for the uses mentioned hereinabove. In order to enhance the patient's comfort, materials have already been proposed which exert a certain soothing effect on the most exposed parts of the skin. Thus a known natural gum called Karaya gum may be formed in a plate-like or an annular pad after moulding with a suitable binder such as glycerine. French Printed Patent Application No. 2,242,115 (Hollester Incorporated) proposes synthetic gums for the same purposes. The gum-based pad member may be put into position to cooperate with the collecting device so as to be maintained in the zone where contact of excretions with the patient's skin may occur. Thus, it has already been suggested, once the gum is in annular configuration, to place the same about the artificial body opening to try to produce an improved connection between it and the collecting device.

This known device is not thoroughly satisfactory. Indeed, the sealing effect around the gum-based annular pad is imperfect. What is worse, the elastic and soothing properties of the gum deteriorate when it bears against the skin around the artificial body opening. In fact, the gum tends to melt at body temperature and dissolves in strong excretions, particularly gastric juices.

U.S. Pat. No. 3,837,342 discloses a device in which a layer of the double-faced adhesive member is applied against the outer part of a bag and covered with a removable protective film. With scissors an opening is cut both in the wall of the bag in the adhesive member and the protective film, the opening being of the required dimension, then the protective film is removed and the adhesive member is placed on the skin at the desired location. Such a modus operandi yields results which largely depend on the manual dexterity of the operator; since the opening necessarily has the same dimension in the wall of the bag and in the protective film, no later alteration is possible, for example to repair an opening which is too big.

An object of the invention consists in an improved device for collecting body excretions which does not have the drawbacks of known prior art devices briefly summarized above.

A more particular object of the invention consists in a device which provides considerable comfort for the user owing to the improved positioning of the gum-based member and its connection with the rest of the device, whilst in addition the device is easily adaptable to artificial body openings of any transverse dimension.

According to the invention there is provided a device for draining and collecting body excretions, comprising a gum-based member adapted to come into contact with skin round the location from which the body excretions are discharged and having a hole enabling the free flow of the excretions, a support on which a bag adapted to collect the excretions is secured, wherein the support made of supple material has an aperture larger than the hole in gum-based member, pre-cut zones concentric with the said aperture for providing apertures of different dimensions adapted for particular needs, the said support being preferably reinforced beyond the pre-cut zones, and wherein the gum-based member is, while the device is being positioned, operatively connected to the support pushing the portion surrounding the hole through the aperture in the support thereby providing a wrap-around pad tightly embracing the portion defining the aperture and the location from which the excretion is discharged.

Generally speaking all the substances as well as the components of the device are of such a nature that they are fully tolerated by the body.

A gum-based member of any substance of natural or synthetic origin may be used which is capable of being produced in compact, malleable paste form.

A suitable natural gum is Karaya gum. It is used in a mixture with a binder such as glycerine to constitute the member in any shape.

It should, however, be noted that in the present device the gum-based member has two functions: (1) a softening or soothing function which is taught in the prior art, and (2) a new function owing to its position in the device which essentially ensures sealing during the draining, discharge or withdrawal of excretion. The gum-based member has in effect its own plasticity which makes it suitable for shaping to form an annular wrap-around pad as will be described hereinafter.

Given the relative requirement of the gum-based member to provide this double function, it may be made of one or more parts. In the latter case, it will then be a composite material having a smooth face and a plastic coating, or a tram, capable of being shaped into an annular wrap-around pad. For the sake of simplicity, it appears that a one-piece Karaya-gum based member will give satisfaction.

The gum-based member cooperates with a support consisting of a supple plastic film or sheet. For positioning, the gum-based member may be stuck directly to the support sheet or deposited thereon by coating.

Alternatively, it is also foreseen that a gum-based member may be carried on a plastic film which then serves as securing means on the support, for example by means of an adhesive or heat welding.

It was previously pointed out that the support comprises a flexible plastic sheet. The choice of the plastic material depends solely on practical considerations of an economic nature, insofar as the plastic sheet employed has a sufficiently plasticity to give the support its suppleness. Another requirement of the plastic material for the support is suitable tearability in the pre-cut zone to allow removal of material without any particular instrument. By way of example of plastic materials for the support sheet, a polyvinyl chloride (PVC) plastisol, a silicone elastomer or a polyamide may be used. We prefer plastified PVC plastisol.

One essential characteristic of the invention is that the support must have an aperture the transverse dimension of which is smaller than that of the apertures which may be produced in the support sheet from the pre-cut zones which are disposed concentrically of the apertures. The dimension of the smallest possible aperture in the support is, in any case, slightly larger than the hole formed in the gum-based member. A fortiori, the apertures of increasing cross dimensions which it is possible to produce from the pre-cut support will be of successively larger dimensions with respect to the hole in the gum-based member.

In parts of the support beyond the pre-cut zones, it is practically indispensable to reinforce the support with a web of synthetic or natural material; it has been found that the use of a web of natural material such as cotton, being more absorbant that plastisols, is advantageous. By way of example the web used is preferably a cotton poplin. It is also important for the support to remain supple so that the device is essentially a composite member of the gum-based member and the support which retains substantially the plastic properties of the gum. The parts of the support where the web constitutes a reinforcement is useful for the mechanical strength of the unit and namely for allowing the attachment of straps of a fastening belt passing through holes formed, as is known, in the support.

To provide the pre-cut zones, a clearance of corresponding dimension is made in the web and then in a known manner the support sheet is cut so as to leave only spaced-apart attachment points in the zones. By virtue of the pre-cut zones apertures of any one of a number of suitable diameters may be produced.

The last feature is a considerable importance in practice, because, when the present device is to be put in position round an artificial body opening, one begins by measuring the transverse dimension of the same so the appropriate pre-cut zone in the support can be selected corresponding to this dimension. It is important to stress that the gum-based member is not pre-cut because it has only one hole whose dimension will in any event be smaller than that of the aperture selected for the support. In this way the portion of the gum-based member which is opposite the aperture in the support may be forced through the aperture to form an annular wrap-around pad projecting from the other side of the support. Accordingly, not only this is an excellent operative connection of the gum-based member and the support provided but also excellent sealing is produced around the artificial body opening.

According to another preferred feature the reduced strength lines radially of the hole, e.g. in star formation, may be formed in the gum-based member thereby making it easy to force the gum through the aperture in the support which makes the formation of the annular pad easier.

The present device also comprises, in a known manner, a bag adapted to collect body excretions. This bag may be of any nature whatsoever. It is preferably of plastic material and may be disposable. The bag is secured or fastened to the support, preferably removably, for example by mechanical means (such as snap fasteners), or by an adhesive. Thus a filled bag may be removed and replaced by a new bag leaving the rest of the device in place. This arrangement, likewise known in the prior art, is advantageous for the user, particularly for those who have to use an artificial anus. In special circumstances known emptiable bags may also be secured to the present device.

The device will be illustrated without being limited by the embodiment hereinafter described with reference to the accompanying drawings:

FIG. 1 is a rear view of the embodiment of the device, without the collecting bag;

FIG. 2 is a front view of the device in FIG. 1;

FIG. 3 is a cross-section taken on line III—III in FIG. 1;

Figure 4:
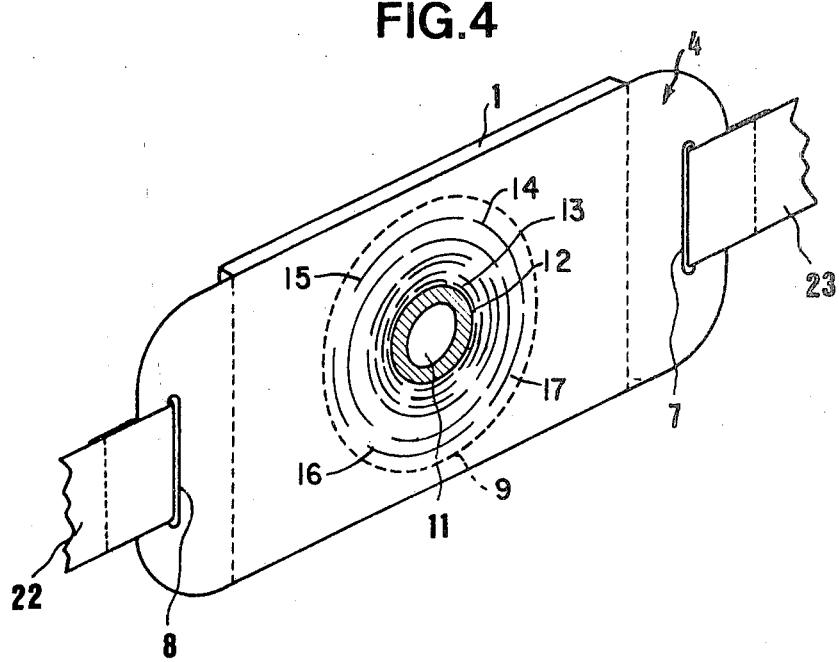
FIG. 4 shows in perspective the device in FIG. 1 provided with a fastening strap or belt.

As shown in the rear view of FIG. 1 the device without its collecting bag comprises a member 1 of a Karaya gum base mixed with glycerine. The member 1 is formed as a flat cushion with a central hole 2 and lines 3 of reduced strength extending radially outwardly from the hole in star formation. The cushion 1 is secured to a support sheet designated by general reference numeral 4. In the illustrated embodiment the gum-based flat member is glued to the support sheet 4.

The support sheet is best viewed in FIG. 2 which is a front view of the device, once again without the collecting bag. The support sheet 4 is made of PVC plastisol with a cotton poplin web along the end portions 5 and 6. Slots 7 and 8 are formed in end portions 5 and 6 for receiving straps of a fastening belt. The reinforcement 9 is clearly visible in FIG. 3 showing the device in section.

According to a main feature of the invention, in the present embodiment the support sheet shown in FIG. 2 has a central aperture 11 whose diameter is greater than that of the hole in the gum-based flat member 1. The hole 11 is surrounded with concentric zones 12, 13 and the like which are defined by pre-cut lines. In the illustrated embodiment the pre-cut lines are circular. By way of example, a pre-cut line comprises four circular segments 14, 15, 16 and 17. The sheet-like support material is thus pre-cut except at attachment points 18, 19, 20 and 21. The other pre-cut zones are defined in the same manner. The pre-cut lines are manually tearable or severable by hand without need of any special instrument.

FIG. 4 is a perspective view which shows, diagrammatically, how the device is put in place with a fastening belt of which straps 22 and 23 pass through holes or slots 7 and 8 in the support sheet 4. The gum-based flat member 1 is in contact with the patient's body. The hole 11 faces the place where the body excretion is to be drained or drawn off. The collecting bag not illustrated is secured to the support sheet to the side visible in FIG. 4.

Figure 6:
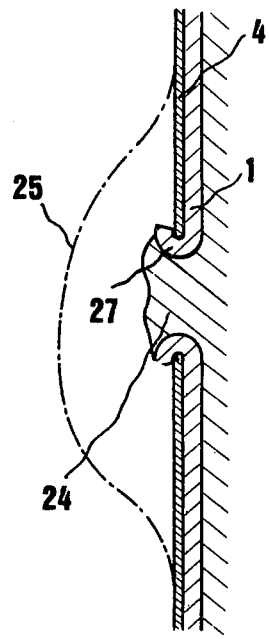
FIG. 6 is a cross-sectional view on an enlarged scale similar to FIG. 5 but after the device is put into position round the artificial body opening.
Figure 5:
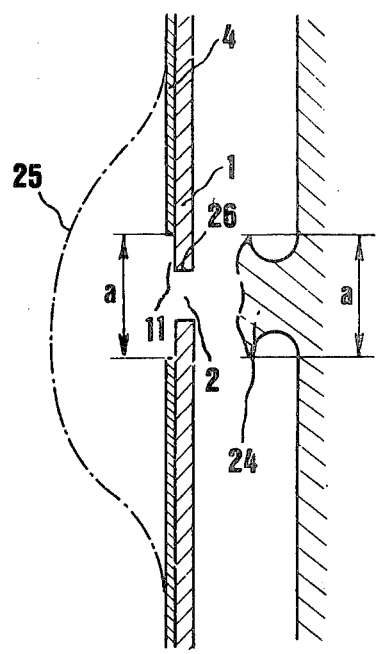
FIG. 5 is a cross-sectional view on a larger scale of a anastomosis or artificial body opening before the device is in position thereon.

FIGS. 5 and 6 illustrate, in more detailed fashion, the particularities of the positioning of the device, for example, in case of the artificial body opening for an artificial anus. FIG. 5 shows the device before it is put into place. The artificial body opening is shown schematically at 24. It has a transverse dimension $a$. The central aperture 11 having a diameter which corresponds to the transverse dimension $a$ is provided in the support sheet 4. This is effected simply, by hand, thanks to the pre-cut lines in the support sheet 4. The collecting bag is schematically illustrated in the dash-dotted line 25.

The placing of the device in position is illustrated in FIG. 6. To this end the portion 26 of the flat member 1 is pushed, preferably by hand, through the aperture 11 to form an annular wrap-around pad portion 27 which tightly embraces the artificial body opening 24, while at the same time bearing accurately against the edge of the aperture 11. Thus, not only is enhanced comfort achieved for the user but also added manipulability of the device. It will be recognized by reference to FIG. 5 that the drawbacks of the prior art devices are eliminated by the present invention. In fact, according to the known technique, the size of the aperture 11 was not selected as a function of the size of the artificial opening 24 in such a manner that the positioning of the gum-based flat member was not accurate. Leaking of excretions between the flat member 1 and the patient's body ensued which after a while made the wearing of the device intolerable for the user.

FIGS. 5 and 6 also illustrate various constituent parts of the invention.

What we claim is:

1. A device for draining and collecting body excretions, comprising a gum-based flat, plate-like member adapted to come into contact with the user's skin round the location from which excretion is to be discharged having a hole enabling the free flow of excretion therethrough and lines of reduced strength extending radially outwardly from said hole, a support on which a bag for collecting excretion is adapted to be secured, the support being of supple material and having an aperture larger than the hole in the gum-based member and annular zones concentric with said aperture and secured to said support by manually tearable attachment points for enlarging the size of said aperture in said support by removal of at least one of said annular zones, the gum-based member being operatively connected to the support by pushing the portion of the member surrounding the hole having said lines of reduced strength through said aperture and around the edge of said aperture in the support when positioning the device on the user, thereby forming a wrap-around pad tightly embracing and sealing said edge of the aperture and the location from which the excretion is discharged when in position on the user.

2. A device according to claim 1, wherein the gum-based member is capable of being provided in a compact malleable form.

3. A device according to claim 2, wherein the gum-based member is made of Karaya gum mixed with a binder.

4. A device according to claim 3, wherein the binder is glycerine.

5. A device according to claim 1, wherein said supple material for the support is selected from the group comprising polyvinyl chloride plastisol, silicone elastomer and polyamide.

6. A device according to claim 1, wherein said support has an aperture smaller than the apertures which may be provided in the support by punching out the said zones concentric with the aperture, the size of the smallest aperture in the support being slightly greater than the hole in the gum-based member.

7. A device according to claim 1, wherein the support is reinforced beyond the said zones.

8. A device according to claim 7, wherein the support is reinforced with a web of fabric.

9. A device according to claim 8, wherein the fabric is cotton poplin.

10. A device according to claim 7, wherein the web reinforced portions of said support have openings for receiving straps of a fastening belt for securing the device on the user's body.

11. A device according to claim 1 further comprising a disposable bag for collecting body excretions securable to the support.

12. A device according to claim 11, wherein said collecting bag is removably securable to said support by mechanical means.

13. A method of utilizing round an artificial body opening a device comprising a gum-based flat, plate-like member adapted to come into contact with the user's skin having a hole enabling the free flow of excretion therethrough and lines of reduced strength extending radially outwardly from said hole, a support on which a bag for collecting excretion is adapted to be secured, said support being of supple material and having an aperture larger than the hole in the gum-based member and annular zones concentric with said aperture and secured to said support by manually tearable attachment points for enlarging the size of said aperture in said support by removal of at least one of said zones, comprising the steps of measuring the transverse dimension of said artificial body opening, selecting a said zone in said support corresponding to the transverse dimension measured, pushing out all smaller annular zones to form the desired aperture in said support, forcing the portion surrounding the hole in said member and opposite said aperture through said aperture and around the edge of said aperture thereby providing an annular wrap-around pad extending through said aperture to the other side of said support, and thereafter placing said device into position on the user with said gum-based member in contact with the user's skin, the annular wrap-around pad tightly embracing and sealing the portion surrounding said artificial body opening.

* * * * *